(12) United States Patent
Albritton, IV et al.

(10) Patent No.: US 11,918,196 B2
(45) Date of Patent: Mar. 5, 2024

(54) APPARATUS, SYSTEM AND METHOD FOR CONTROLLING THE POSITION OF AND PROVIDING SUCTION IN A SURGICAL CATHETER OR GUIDE

(71) Applicant: Ford Albritton, IV, Dallas, TX (US)

(72) Inventors: Ford Albritton, IV, Dallas, TX (US); Bryan Thomas Lunsford, Galveston, TX (US)

(*) Notice: Subject to any disclaimer, the term of this patent is extended or adjusted under 35 U.S.C. 154(b) by 290 days.

(21) Appl. No.: 17/583,770

(22) Filed: Jan. 25, 2022

(65) Prior Publication Data
US 2022/0143370 A1 May 12, 2022

Related U.S. Application Data

(63) Continuation of application No. 16/568,640, filed on Sep. 12, 2019, now Pat. No. 11,229,782, which is a continuation of application No. 14/691,438, filed on Apr. 20, 2015, now Pat. No. 10,413,714, which is a continuation of application No. 12/454,560, filed on May 18, 2009, now Pat. No. 9,011,412.

(60) Provisional application No. 61/127,848, filed on May 16, 2008.

(51) Int. Cl.
| | |
|---|---|
| *A61B 17/00* | (2006.01) |
| *A61M 1/00* | (2006.01) |
| *A61M 25/00* | (2006.01) |
| *A61M 25/01* | (2006.01) |
| *A61M 25/06* | (2006.01) |
| *A61M 25/09* | (2006.01) |
| *A61M 39/10* | (2006.01) |
| *A61B 17/22* | (2006.01) |
| *A61B 17/34* | (2006.01) |

(52) U.S. Cl.
CPC .............. *A61B 17/00* (2013.01); *A61M 1/74* (2021.05); *A61M 1/80* (2021.05); *A61M 25/0097* (2013.01); *A61M 25/01* (2013.01); *A61M 25/0136* (2013.01); *A61M 25/0662* (2013.01); *A61M 25/09* (2013.01); *A61M 39/10* (2013.01); *A61B 17/00234* (2013.01); *A61B 2017/0042* (2013.01); *A61B 2017/00424* (2013.01); *A61B 2017/00469* (2013.01); *A61B 2017/22049* (2013.01); *A61B 17/3415* (2013.01); *A61B 2217/005* (2013.01); *A61M 1/84* (2021.05); *A61M 2025/09116* (2013.01); *A61M 2039/1077* (2013.01)

(58) Field of Classification Search
CPC ........ A61B 17/3415; A61B 2017/0042; A61B 2017/00424; A61B 2017/00469; A61B 2217/005; A61M 1/0086; A61M 2039/1077; A61M 25/0136; A61M 39/10
See application file for complete search history.

*Primary Examiner* — Deanna K Hall
(74) *Attorney, Agent, or Firm* — Bell Nunnally & Martin LLP

(57) ABSTRACT

Systems and methods are disclosed that include a guide catheter apparatus insertable through an external body passage of a subject. The guide catheter apparatus includes a substantially rigid shaft and a handle. The shaft has a proximal opening, a distal opening, and a lumen extending between the proximal opening and the distal opening. The handle has a structure to allow a position of the guide catheter to be controlled by some or all of three fingers of one hand of an operator of the handle. The structure of the handle is adapted to permit the operator to position a thumb and index finger of the hand to manipulate a working device inserted into the lumen of the guide catheter, where the working device is manipulable via a portion of the working device immediately adjacent to the handle.

20 Claims, 3 Drawing Sheets

APPARATUS, SYSTEM AND METHOD FOR CONTROLLING THE POSITION OF AND PROVIDING SUCTION IN A SURGICAL CATHETER OR GUIDE

CROSS-REFERENCE TO RELATED APPLICATION(S) AND CLAIM OF PRIORITY

The present application is a continuation of U.S. application Ser. No. 16/568,640 filed Sep. 12, 2019, now U.S. Pat. No. 11,229,782, which is a continuation of U.S. application Ser. No. 14/691,438 filed Apr. 20, 2015, now U.S. Pat. No. 10,413,714, which is a continuation of U.S. application Ser. No. 12/454,560 filed May 18, 2009, now U.S. Pat. No. 9,011,412, which claims the benefit under 35 U.S.C. § 119(e) of U.S. Provisional Patent Application No. 61/127,848 filed May 16, 2008, each of which are incorporated herein by reference in their entirety as if fully set forth herein.

TECHNICAL FIELD

The present invention is generally directed to surgical devices and, in particular, to an apparatus, system and method for manipulating a surgical catheter and working device with a single hand.

BACKGROUND

FIG. 1 presents a schematic diagram of a typical surgical catheter (or guide) 100 that may be used to perform a procedure in a nasal, sinonasal, or oral passage or other external body passage. The catheter 100 includes a tube 102 having therein a duct 104. The tube 102 may be introduced into the body passage and a guidewire or other working device inserted into the duct 104 via an opening 106 at a proximal end of the catheter 100. The duct 104 then operates to guide the working device to an opening 108 at a distal end of the tube 102. A handle 110 may be formed into or attached to the proximal end of the tube 102 to permit positioning of the catheter 100 by movement of the catheter 100 into and out of the body passage and rotation of the catheter 100 around a longitudinal axis with a first hand. Once a desired position is obtained, the catheter 100 with fingers of a second hand that also grasps an endoscope and held in position. The first hand may then be used to manipulate the working device inserted into the duct 104.

SUMMARY

This disclosure provides an apparatus, system and method for manipulating a surgical catheter and working device with a single hand.

In one embodiment, a system includes a guide catheter, a working device and a handle coupled to the guide catheter. The guide catheter is insertable through an external body passage of a subject, and includes a substantially rigid shaft, a proximal opening, a distal opening and a lumen extending between the proximal opening and the distal opening. The working device is adapted to be insertable through the lumen of the guide catheter. The handle has a structure that allows a position of the guide catheter to be controlled by some or all of three fingers of one hand of an operator of the handle. The structure of the handle is adapted to permit the operator to position a thumb and index finger of the hand to manipulate the working device via a portion of the working device that is immediately adjacent to the handle.

In another embodiment, a method includes inserting a guide catheter through an external body passage of a subject, inserting a working device through the lumen of the guide catheter, and controlling a position of the guide catheter using a handle affixed to the guide catheter while substantially simultaneously manipulating the working device. The position of the guide catheter is controlled by some or all of three fingers of a hand and a thumb and index finger of the hand manipulate the working device via a portion of the working device immediately adjacent to the handle.

In still another embodiment, a guide catheter apparatus insertable through a external body passage of a subject includes a substantially rigid shaft and a handle. The shaft has a proximal opening, a distal opening, and a lumen extending between the proximal opening and the distal opening. The handle has a structure to allow a position of the guide catheter to be controlled by some or all of three fingers of one hand of an operator of the handle. The structure of the handle is adapted to permit the operator to position a thumb and index finger of the hand to manipulate a working device inserted into the lumen of the guide catheter, where the working device is manipulable via a portion of the working device immediately adjacent to the handle.

BRIEF DESCRIPTION OF THE DRAWINGS

For a more complete understanding of the present invention and its advantages, reference is now made to the following description taken in conjunction with the accompanying drawings, in which.

DETAILED DESCRIPTION

Figure 1:
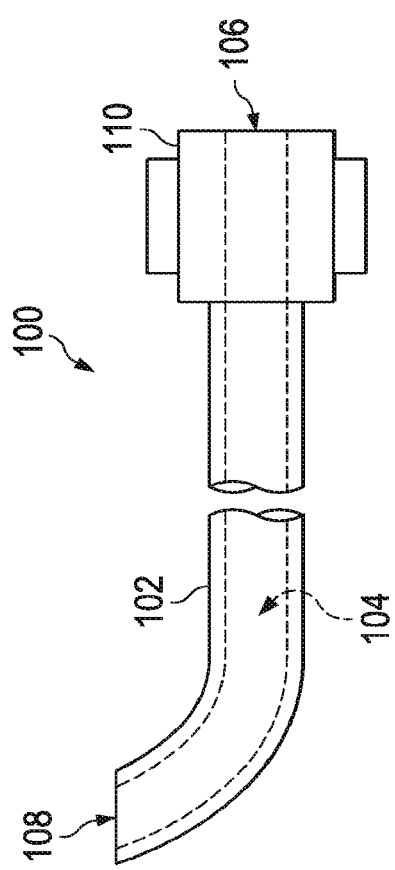
FIG. 1 presents a schematic diagram of a surgical catheter.
Figure 2:
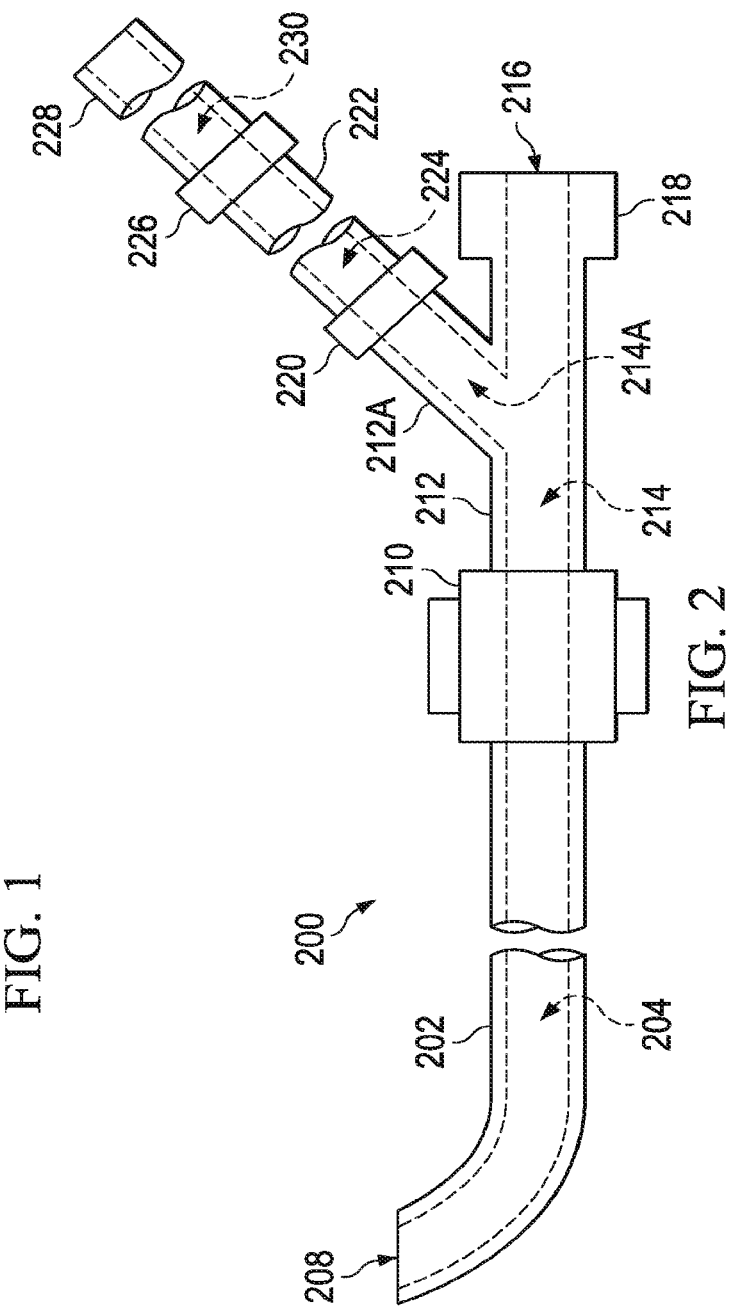
FIG. 2 presents a schematic diagram of a surgical catheter according to this disclosure.

FIG. 2 depicts a schematic diagram of a surgical catheter 200 according to the present disclosure. The catheter 200 includes a tube 202 having therein a duct 204 with an opening 208 at a distal end. A handle 210 may be formed into or attached to the proximal end of the tube 202. A Y-shaped section 212 is coupled to a proximal end of the tube 202 at a distal end of the section 212. The section 212 includes a second handle 218 and an opening 216 at a proximal end of the section 212. The section 212 includes a duct 214 that mates with the duct 204 of the tube 202. As described for the catheter 100, working devices may be inserted in the opening 216 and guided to the opening 208 at the distal end of the tube 202 by the duct 214 and the duct 204.

The section 212 further includes a branch section 212A having a branch duct 214A. Suction may be applied to the catheter 200 via the branch section 212A. Where both the opening 216 and the opening 208 are left uncovered, the suction will be conducted to the opening 216 via the ducts 214A and 214 and to the opening 208 via the ducts 214A, 214 and 204. Because the tube 202 is inserted into a body passage and, possibly, through a hole in a membrane of the body, the opening 208 may be sealed off from the ambient air pressure outside the catheter 200. In such a situation, the suction applied to the branch section 212A will primarily result in air being drawn through the opening 216 and into the duct 214A.

Partially or completely blocking the opening 216, however, will result in the suction drawing blood, mucous, and other materials into the opening 208 and along the ducts 204, 214 and 214A, resulting in removal of the materials from the vicinity of the distal end of the tube 202. An operator of the catheter 200 may vary the mount of blockage of the opening 216 with a finger or valve, in order to control the amount of suction delivered to the opening 208. In this way, materials produced by the body in response to operation of the working devices (or freed from the body by the operation of the working devices) may be removed from vicinity of the distal end of the tube 202 by way of a controlled amount of suction. Such removal may provide a clearer view for an endoscope inserted into the catheter 200, a clearer working area for a cutter, or other similar benefits.

A coupling 220 at a proximal end of the branch section 212A couples a tube 222 having a duct 224 to the branch section 212A and the duct 214A, respectively. The tube 222 may conduct the suction to the section 212 from a suction canister or other suction source. Where the tube 222 is stiff, the coupling 220 may permit rotation of the branch section 212A relative to the tube 222, to reduce interference by the tube 222 with an operator's positioning of the catheter 200.

In another embodiment, a coupling 226 at a proximal end of the tube 222 may couple a second tube 228 having a duct 230 to the tube 222 and the duct 224, respectively. The coupling 220 does not permit rotation of the tube 222 relative to the branch section 214A, nor does the coupling 226 permit rotation of the tube 228 relative to the tube 222. However, where the tube 228 is stiff, a flexible tube 222 may be employed to reduce interference by the tube 228 with an operator's positioning of the catheter 200.

While the section 212 is shown and described as separate from the tube 202, it will be understood that in other embodiments, the section 212 may be formed integrally with the tube 202. In still other embodiments, the coupling 220 may be mounted directly to a side of the section 212, rather than to the branch section 212A. While the section 212 is shown fixedly attached to the tube 202, in other embodiments the section 212 may move relative to the tube 202, in order to further free tethering and increase a user's free and unencumbered movements in space, while leaving the tube 202 in a substantially fixed position relative to the patient's body. In such embodiments, the section 212 may rotate freely or be moved to a desired position and then locked into place via a suitable locking mechanism.

Figure 3:
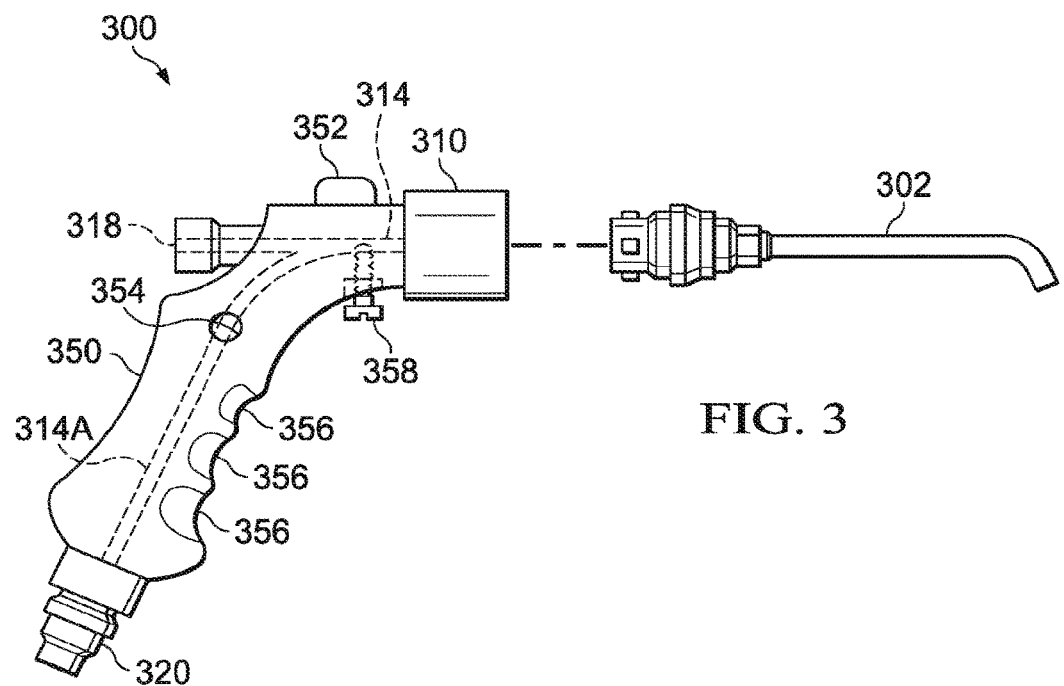
FIG. 3 presents a schematic diagram of another surgical catheter according to this disclosure.

FIG. 3 presents a schematic diagram of a second surgical catheter 300 according to the disclosure. The catheter 300 includes a body having a handle 350. At a distal end of the catheter 300 is a guide coupling 310, which may be a rotating 'female' luer lock. The guide coupling 310 accepts and locks a guide 302. The coupling also operates to permit the guide 302 to be rotated to a desired position relative to the handle 350 and locked in that position for use. The guide coupling 310 may include detents to allow the guide 302 to be positioned only at predetermined positions relative to the handle 350.

The handle 350 may include concavities 356 adapted to provide a secure grip on the handle 350 by some or all of the middle, ring and little fingers of a user's hand, as will be described in greater detail with reference to FIG. 5. The handle 350 may include a protrusion 352 adapted to a secure grip on the handle 350 by a user when the upper portion of the handle 350 is positioned between the middle and ring fingers while grasping the lower portion of the handle 350 with the ring and little fingers.

The handle 350 includes a duct 314 that passes from the guide coupling 310 to an opening 318 at a distal end of the handle 350. The duct 314 is aligned with a duct in the guide 302 when the guide 302 is mounted in the guide coupling 310, so that an endoscope, guidewire or other working device may be inserted into the opening 318, pass through the duct 314 and the guide 302 to emerge from a distal end of the guide 302. A branch section 314a of the duct 314 extends through the handle 350 to a handle coupling 320. A source of suction may be attached to the handle 350 at the handle coupling 320 to provide suction at the distal end of the guide 302, as described with reference to FIG. 2.

Where the opening 318 is provided with a one-way valve to prevent air being drawn into the opening 318 by suction in the branch section 314a, an opening 354 may be provided between the branch section 314a and the exterior of the handle 350 to allow the user to control the amount of suction present at the distal end of the guide 302.

The handle 350 may be provided with a locking screw 358. Once a user has inserted a guide catheter through the duct 314 to a desired position within the patient, the user may operate the locking screw 358 to hold the guide wire in position while inserting another working device, such as a balloon catheter, along the guide wire. Once the second working device reaches the position of the locking screw 358, the locking screw 358 may be operated to withdraw it from the duct 314 and allow the second working device to continue along the duct 314.

Figure 4:
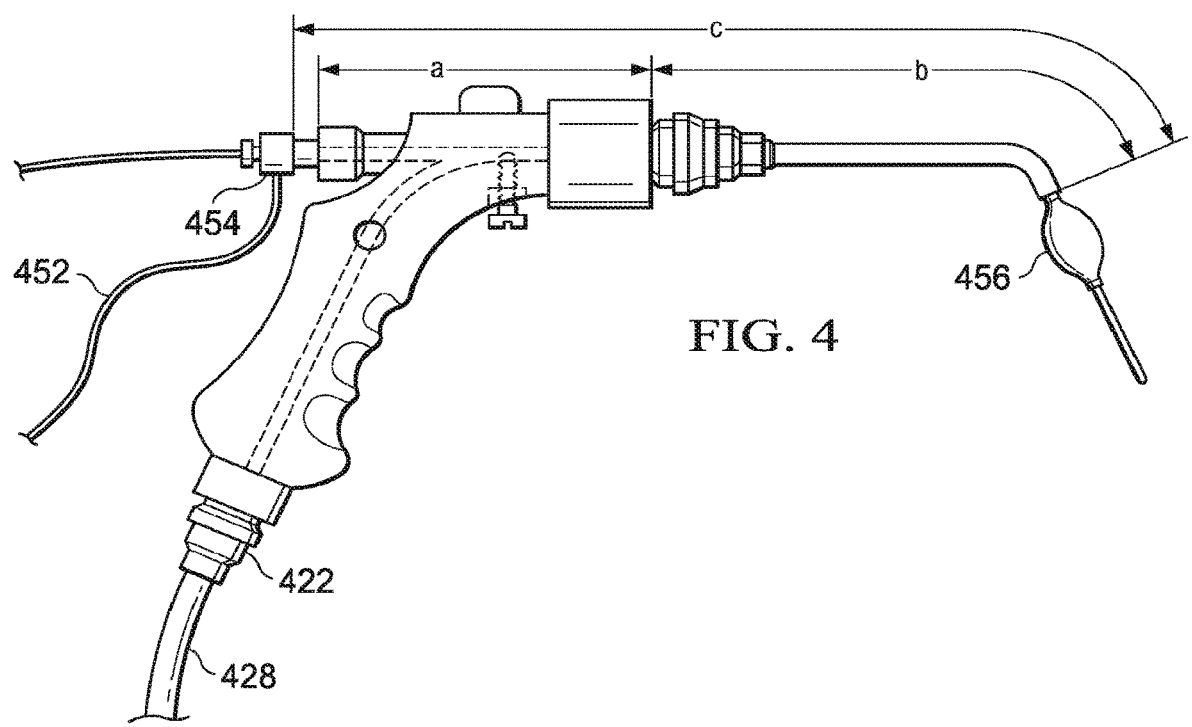
FIG. 4 presents a schematic diagram of a surgical catheter according to this disclosure with working devices inserted.

With reference to FIG. 4, a balloon catheter 454 has been inserted into the opening 318 and through the guide 302. The balloon catheter 454 includes a tube 452 coupled to an inflation device. Operation of the inflation device causes an inflation segment 456 of the balloon catheter 454 to inflate. The handle 350 may be designed so that the distance between the opening 318 and the guide coupling 310 (indicated by the letter a), when added to the length of the guide 302 (indicated by the letter b), totals less than the distance between the attachment of the tube 452 at a proximal end of the balloon catheter 454 and the inflation segment 456 (indicated by the letter c).

Furthermore, the distance between the opening 318 and the guide coupling 310 may be selected based upon a distance between a shoulder feature of the proximal end of the balloon catheter 454 and the inflation segment 456. The distance may be selected to allow the shoulder feature to engage the opening 318 while the inflation segment 456 extends past the distal end of the guide 302 substantially only far enough to inflate without interference from the distal end of the guide 302. In this way, motion of the inflation segment 456 towards or away from the guide 302 during inflation may be minimized to reduce the likelihood that the inflation segment 456 will slip out of position when inflated.

A suction tube 428 may be attached to the handle coupling 320 by a tube coupling 422. Where the suction tube 428 is stiff, the tube coupling 422 (or the handle coupling 320) may be flexible and/or rotate to reduce interference by the stiff tube 428 with positioning the surgical catheter 300.

Figure 5:
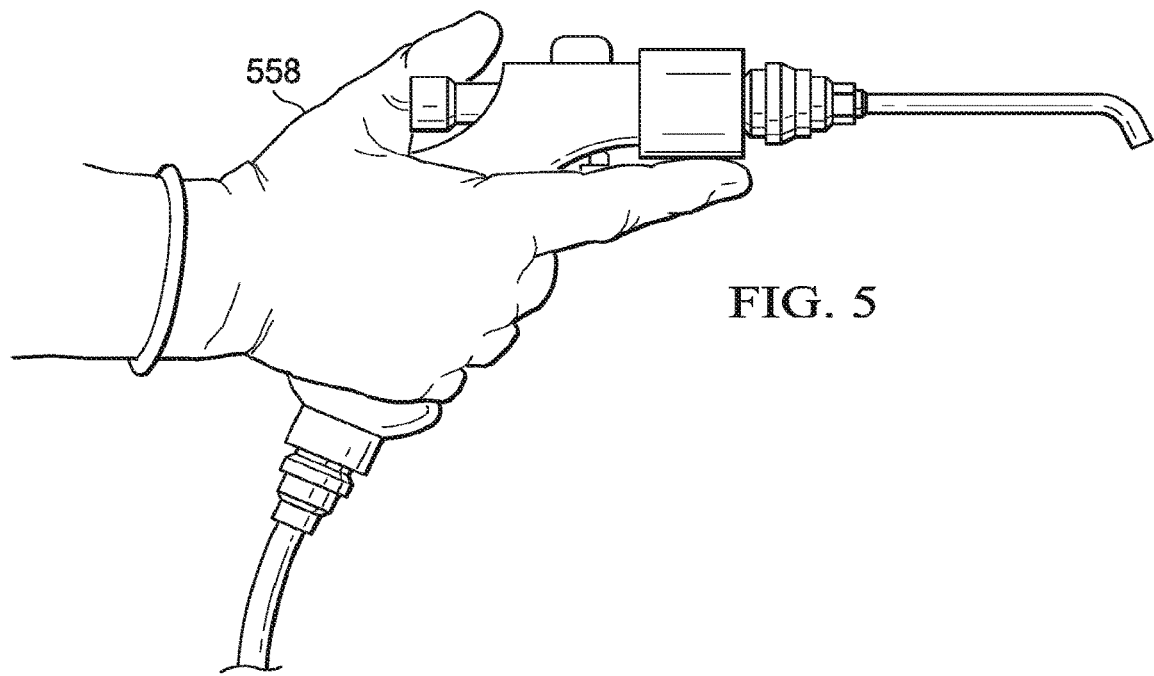
FIG. 5 presents a schematic diagram of a surgical catheter according to this disclosure held by a user.

FIG. 5 illustrates the surgical catheter 300 in use. A surgeon or other user holds the handle 350 in a hand by some or all of the small finger, the ring finger and the middle finger. Gripped in this way, the surgeon may move the guide 302 in the direction of its longitudinal axis, may rotate the guide 302 about its longitudinal axis, or may rotate the guide 302 about an axis other than its longitudinal axis ('yaw'). The fore finger and thumb are left free to manipulate a working device inserted into the opening 318 or to cover the opening 318 to redirect suction to the distal end of the guide 302, as described with reference to FIG. 2. As described with reference to FIG. 4, flexibility and/or rotation of the couplings 320 and/or 422 may reduce the interference of a stiff suction tube 428 on such motion.

The lower portion of the handle 350, which is grasped by the fingers, makes an angle with the upper portion of the handle, and with the guide 302, that facilitates the user's manipulation of working devices with the thumb and forefinger of a hand while grasping the handle with some or all of the remaining fingers of the hand. That is, the angle may be selected to place the user's thumb and forefinger in comfortable proximity to the opening 318, and the handle shaped to permit easy motion of the thumb and forefinger towards and away from the opening 318 while securely grasping a working device inserted through the handle 350 into the guide 302. As shown in the figures, that angle may be approximately sixty (60) degrees, although other angles that are less than ninety (90) degrees and more than zero (0) degrees may be employed.

Using the handle 350, the user is enabled to control the position of the guide 302 by positioning the arm and wrist of the hand that is grasping the handle, while simultaneously controlling the position of a working device inserted into the guide 302 with the thumb and forefinger of the same hand. This leaves the user's other hand free for other activities, such as holding an endoscope in position to view the distal ends of the guide 302 and the working device. In this way, the user is able to simultaneously control the position of the distal end of the guide 302 adjacent to a desired region of the patient and manipulate the working device with one hand.

Figure 6:
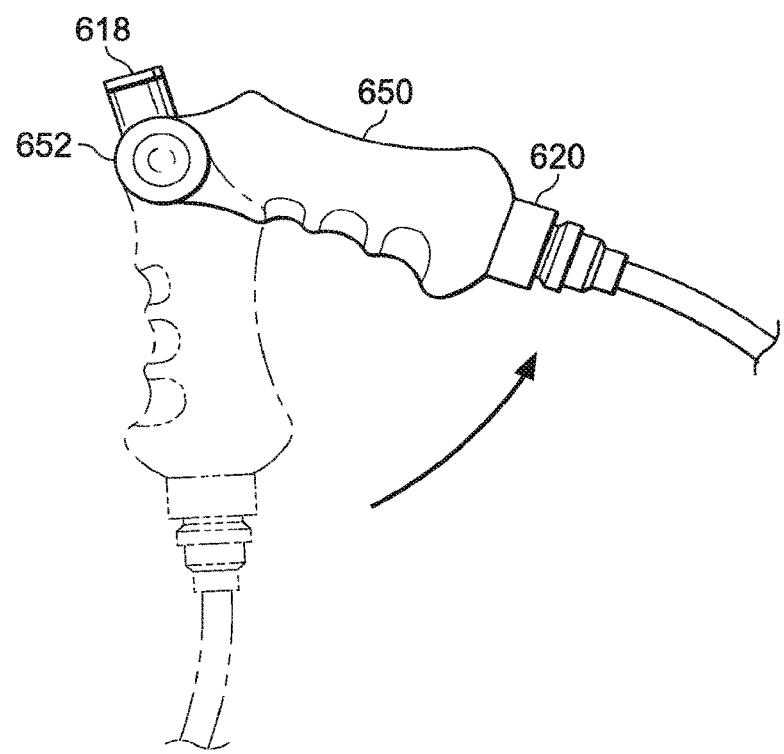
FIG. 6 presents a schematic diagram of still another surgical catheter according to this disclosure.

FIG. 6 illustrates a handle 650 according to the present disclosure wherein the upper portion of the handle 650 comprises a pivot 652. The upper portion includes an opening 618 and a main duct and guide coupling (not shown, but similar to the duct 314 and the guide coupling 310) are in a fixed position relative to each other and to the pivot 652. The duct branch in the handle 650 (not shown, but similar to the branch duct 314a) is pivotally coupled to the main duct, to allow suction applied to a handle coupling 620 to be applied to the opening 318 and a guide attached to the guide coupling. The pivot 652 allows the handle 650 to be rotated to a desired angular position relative to the upper portion and locked into the desired position.

Although the present invention and its advantages have been described in the foregoing detailed description and illustrated in the accompanying drawings, it will be understood by those skilled in the art that the invention is not limited to the embodiment(s) disclosed but is capable of numerous rearrangements, substitutions and modifications without departing from the spirit and scope of the invention as defined by the appended claims.

What is claimed is:

1. A system, comprising:
    a guide catheter insertable through an external body passage of a subject, said guide catheter having a substantially rigid shaft, a proximal opening, a distal opening and a lumen extending between the proximal opening and the distal opening;
    a handle coupled to the guide catheter, the handle having a handle opening, a handle coupling and a structure, wherein the structure is configured to allow a position of the guide catheter to be controlled by some or all of three fingers of one hand of an operator of the handle, wherein the handle opening is configured to couple a tube to an inflation segment at a distal end of the lumen, and wherein the handle coupling is configured to couple a source of suction to a duct through the handle, wherein the handle has a suction opening between the duct and an exterior of the handle to allow the operator to control an amount of suction; and
    a guide wire extending through the lumen of the guide catheter,
    wherein the structure of the handle is adapted to permit the operator to position a thumb or index finger of the hand to move the inflation segment towards or away from the handle and to control, by one of the thumb or index finger, an amount of suction by covering the suction opening to redirect suction from the suction opening towards the guide catheter.

2. The system of claim 1, wherein a longitudinal axis of the handle forms an angle with a longitudinal axis of the guide catheter of less than ninety degrees and more than zero degrees.

3. The system of claim 1, wherein the handle comprises a lower portion and an upper portion where the lower portion and the upper portion are at an angle.

4. The system of claim 1, wherein operation of an inflation device coupled to the tube causes the inflation segment to inflate.

5. The system of claim 1, wherein the suction opening extends from the exterior of the handle to a path of a flow of suction through the duct.

6. The system of claim 1, wherein the handle coupling is further adapted to allow movement of the source of suction relative to the handle.

7. The system of claim 1, wherein the guide catheter is movable relative to the handle.

8. A method comprising:
    inserting a guide catheter through an external body passage of a subject, wherein the guide catheter is coupled to a handle and comprises a substantially rigid shaft, a proximal opening, a distal opening and a lumen extending between the proximal opening and the distal opening;
    coupling a source of suction to a duct through the handle, wherein the handle has a suction opening between the duct and an exterior of the handle;
    coupling a tube to a handle opening, the tube being coupled to an inflation device, wherein operation of the inflation device causes an inflation segment at a distal end of the lumen to inflate;
    controlling a position of the guide catheter using the handle that is formed to allow the position of the guide catheter to be controlled by some or all of three fingers of a hand, while substantially simultaneously using a thumb or index finger of the hand to cause the inflation segment to move towards or away from the handle; and
    controlling the position of the guide catheter using the handle, while substantially simultaneously controlling, by one of the thumb or index finger, an amount of suction by partially or completely covering the suction opening to redirect suction from the suction opening towards the guide catheter.

9. The method of claim 8, further comprising inserting a working device through the handle and the lumen of the guide catheter.

10. The method of claim 8, further comprising operating the inflation device coupled to the tube to inflate the inflation segment.

11. The method of claim 8, wherein controlling the amount of suction comprises partially or completely blocking the suction opening with the thumb or index finger of the hand to cause the suction to draw blood, mucous, or other materials through the duct to remove the blood, mucous, or other materials from a vicinity near the distal end of the guide catheter.

12. The method of claim 8, wherein the suction opening extends from the exterior of the handle to a path of a flow of suction through the duct.

13. The method of claim 8, further comprising coupling the handle to the guide catheter.

14. A guide catheter apparatus insertable through an external body passage of a subject, comprising:
   a substantially rigid shaft with a proximal opening, a distal opening, and a lumen extending between the proximal opening and the distal opening;
   a guide wire extending through the lumen of the guide catheter; and
   a handle coupled to the shaft, the handle having a handle opening, a handle coupling and a structure, wherein the structure is configured to allow a position of the guide catheter apparatus to be controlled by some or all of three fingers of one hand of an operator of the handle, wherein the handle opening is configured to couple a tube to an inflation segment at the distal opening of the lumen, wherein the handle coupling is configured to couple a source of suction to a duct through the handle, wherein the handle has a suction opening between the duct and an exterior of the handle to allow the operator to control an amount of suction, wherein the structure of the handle is adapted to permit the operator to position a thumb or index finger of the hand to move the inflation segment towards or away from the handle, and wherein the structure of the handle is configured to permit the operator to control, by one of the thumb or index finger, an amount of suction by covering the suction opening to redirect suction from the suction opening towards the guide catheter.

15. The apparatus of claim 14, wherein a longitudinal axis of the handle forms an angle with a longitudinal axis of the guide catheter of less than ninety degrees and more than zero degrees.

16. The apparatus of claim 14, wherein the handle comprises a lower portion and an upper portion where the lower portion and the upper portion are at an angle.

17. The apparatus of claim 14, wherein operation of an inflation device coupled to the tube causes the inflation segment to inflate.

18. The apparatus of claim 14, wherein the suction opening extends from the exterior of the handle to a path of a flow of suction through the duct.

19. The apparatus of claim 14, wherein the handle coupling is further adapted to allow movement of the source of suction relative to the handle.

20. The apparatus of claim 14, wherein the guide catheter is movable relative to the handle.

* * * * *